US011229681B2

(12) United States Patent
Takada et al.

(10) Patent No.: US 11,229,681 B2
(45) Date of Patent: Jan. 25, 2022

(54) DOMINANT-NEGATIVE FGF2 ANTAGONISTS

(71) Applicant: The Regents of the University of California, Oakland, CA (US)

(72) Inventors: Yoshikazu Takada, Davis, CA (US); Yoko Takada, Sacramento, CA (US); Seiji Mori, Houston, TX (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/033,007

(22) Filed: Jul. 11, 2018

(65) Prior Publication Data

US 2019/0015478 A1 Jan. 17, 2019

Related U.S. Application Data

(60) Provisional application No. 62/532,511, filed on Jul. 14, 2017.

(51) Int. Cl.
*A61K 38/18* (2006.01)
*C07K 14/50* (2006.01)
*C12N 15/62* (2006.01)
*A61P 35/00* (2006.01)

(52) U.S. Cl.
CPC .......... *A61K 38/1825* (2013.01); *A61P 35/00* (2018.01); *C07K 14/50* (2013.01); *C12N 15/62* (2013.01); *C07K 14/501* (2013.01); *C07K 14/503* (2013.01); *C07K 2319/00* (2013.01)

(58) Field of Classification Search
None
See application file for complete search history.

(56) References Cited

U.S. PATENT DOCUMENTS

| 5,604,293 A * | 2/1997 | Fiddes | C07K 14/501 |
| | | | 530/399 |
| 6,083,706 A * | 7/2000 | Florkiewicz | A61K 31/00 |
| | | | 435/184 |
| 7,186,526 B2 * | 3/2007 | Fiddes | A61K 38/1825 |
| | | | 435/243 |
| 8,168,591 B2 * | 5/2012 | Takada | C07K 14/501 |
| | | | 514/9.1 |

FOREIGN PATENT DOCUMENTS

EP 0 645451 * 3/1995

OTHER PUBLICATIONS

Mori, et al. "The integrin-binding defective FGF2 mutants potently suppress FGF2 signalling and angiogenesis." Bioscience reports 37, No. 2 (2017): BSR20170173.

* cited by examiner

*Primary Examiner* — Marianne P Allen
(74) *Attorney, Agent, or Firm* — Kilpatrick Townsend & Stockton LLP

(57) ABSTRACT

The present invention provides dominant negative mutants of FGF2 for suppressing FGF-mediated cellular signaling. Related compositions, methods, and kits are disclosed.

15 Claims, 6 Drawing Sheets

Specification includes a Sequence Listing.

Docking model (αvβ3)

Adhesion (K562, αvβ3-, α5β1+)

SPR (WT FGF2/αvβ3)

SPR (K125E FGF2/αvβ3)

ERK1/2 activation

DNA synthesis (NIH3T3)

ERK1/2 activation (HUVEC)

Migration (HUVEC)

Tube formation (HUVEC)

Branching points

Aorta ring assay

Sprouting

SEQUENCE LISTING

<160> NUMBER OF SEQ ID NOS: 4

<210> SEQ ID NO 1
<211> LENGTH: 146
<212> TYPE: PRT
<213> ORGANISM: Homo sapiens

<400> SEQUENCE: 1

Pro Ala Leu Pro Glu Asp Gly Gly Ser Gly Ala Phe Pro Pro Gly His
1               5                   10                  15

Phe Lys Asp Pro Lys Arg Leu Tyr Cys Lys Asn Gly Gly Phe Phe Leu
            20                  25                  30

Arg Ile His Pro Asp Gly Arg Val Asp Gly Val Arg Glu Lys Ser Asp
        35                  40                  45

Pro His Ile Lys Leu Gln Leu Gln Ala Glu Glu Arg Gly Val Val Ser
    50                  55                  60

Ile Lys Gly Val Cys Ala Asn Arg Tyr Leu Ala Met Lys Glu Asp Gly
65                  70                  75                  80

Arg Leu Leu Ala Ser Lys Cys Val Thr Asp Glu Cys Phe Phe Phe Glu
                85                  90                  95

Arg Leu Glu Ser Asn Asn Tyr Asn Thr Tyr Arg Ser Arg Lys Tyr Thr
            100                 105                 110

Ser Trp Tyr Val Ala Leu Lys Arg Thr Gly Gln Tyr Lys Leu Gly Ser
        115                 120                 125

Lys Thr Gly Pro Gly Gln Lys Ala Ile Leu Phe Leu Pro Met Ser Ala
    130                 135                 140

Lys Ser
145

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This sequence may encompass 5-10 residues

<400> SEQUENCE: 2

His His His His His His His His His His

```
<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 3

His His His His His His
1               5

<210> SEQ ID NO 4
<211> LENGTH: 10
<212> TYPE: PRT
<213> ORGANISM: Homo sapiens

<400> SEQUENCE: 4

Lys Arg Thr Gly Gln Tyr Lys Leu Gly Ser
1               5                   10
```

US 11,229,681 B2

DOMINANT-NEGATIVE FGF2 ANTAGONISTS

RELATED APPLICATIONS

This application claims priority to U.S. Provisional Patent Application No. 62/532,511, filed Jul. 14, 2017, the contents of which are hereby incorporated by reference in the entirety for all purposes.

STATEMENT AS TO RIGHTS TO INVENTIONS MADE UNDER FEDERALLY SPONSORED RESEARCH OR DEVELOPMENT

This invention was partially supported by NIH Grant No. R33CA196445. The Federal Government may have certain rights to this invention.

REFERENCE TO SUBMISSION OF A SEQUENCE LISTING AS A TEXT FILE

The Sequence Listing written in file 081906-1096074-225910US_SL.txt created on Aug. 31, 2018, 2,295 bytes, ASCII format, is hereby incorporated by reference in its entirety for all purposes.

BACKGROUND OF THE INVENTION

Angiogenesis, formation of new blood vessels from existing vessels, is required for tumor growth and chronic inflammation and a major target for drug discovery. Fibroblast growth factor-1 (FGF1, acidic FGF) and FGF2 (basic FGF) are potent angiogenic agents and have been extensively studied. Therapeutics targeting FGFs (e.g., antibodies and kinase inhibitors to FGF receptors [FGFR]) are not in the clinic yet. The finding that integrin antagonists inhibit FGF2-induced angiogenesis suggested that integrins are involved in FGF signaling through crosstalk. It was discovered that FGF1 and FGF2 directly bind to integrins (e.g., αvβ3) and induce formation of the integrin/FGF/FGFR complexes on the cell surface (designated the ternary complex model). The ternary complexes have been detected by co-immunoprecipitation. FGF mutants defective in integrin binding are defective in signaling and ternary complex formation, but still bind to FGFR, suggesting that the binding of FGF to FGFR is not sufficient to induce FGF signals. Study results suggest that integrins are coreceptors common to FGF and other growth factors and positively regulate FGF signaling. Based on the hypothesis that the FGF2 mutants (or FGF2 decoys) can function as potent antagonists to signal transduction, the present inventors designed and tested such FGF2 decoys and observed that FGF2 decoys potently suppress angiogenesis in vivo. It is therefore concluded that these mutants have important applications as therapeutics due to their capability to effectively suppress angiogenesis and tumor growth.

BRIEF SUMMARY OF THE INVENTION

In one aspect, the present invention provides an isolated polypeptide acting as an antagonist of FGF2, i.e., capable of suppressing FGF2-mediated cellular signaling, as well as downstream events such as ERK1/2 activation, cell proliferation, and angiogenesis. This isolated polypeptide comprises the amino acid sequence of SEQ ID NO:1, wherein the amino acid sequence of SEQ ID NO:1 has at least one mutation at residue(s) K119, R120, or K125, and wherein the polypeptide suppresses FGF2 signaling, as verified by assay methods known in the pertinent field and/or described herein. In some embodiments, the polypeptide consists of the amino acid sequence of SEQ ID NO:1, with at least one amino acid at K119, R120, or K125 of the amino acid sequence of SEQ ID NO:1 mutated, and the polypeptide suppresses FGF2 signaling. In some embodiments, the amino acid sequence of SEQ ID NO:1 has K119 mutated such as by deletion or substitution, for example, the mutation is K119E. In some embodiments, the amino acid sequence of SEQ ID NO:1 has R120 mutated such as by deletion or substitution, for example, the mutation is R120E. In some cases, both K119 and R120 in SEQ ID NO:1 are mutated such as by deletion or substitution, for example, the mutations are K119E and R120E. In some embodiments, the amino acid sequence of SEQ ID NO:1 has K125 mutated by deletion or substitution, for example, the mutation is K125E. In some cases, the mutations are K119E/R120E/K125E. In some embodiments, the FGF2 mutant polypeptide includes, in addition to SEQ ID NO:1 the FGF2 derived amino acid sequence, at least one possibly two amino acid sequences heterologous to FGF2 in origin and located at the N-terminus and/or C-terminus of the polypeptide. In some cases, non-naturally occurring amino acids or amino acid analogs (such as one or more D-amino acids) may be present in an FGF2 mutant polypeptide.

In a related aspect, this invention provides a composition for suppressing FGF2 signaling, especially for use in treating conditions or diseases where undesired inflammation or angiogenesis is present, for example, in cancer treatment. The composition comprises the FGF2 mutant polynucleotide described above and herein plus a physiologically acceptable carrier. In some embodiments, the composition further includes one or more anti-cancer agent, including anti-angiogenic agent(s) such as CB3988, WEB 2086, INF-2α, TNP-470, endostatin, SU 5416, SU 6668, batimistat, angiostatin, and celecoxib.

In a second aspect, the invention provides a method for suppressing FGF2-mediated cellular signaling and therefore downstream events such as ERK1/2 activation, cell proliferation, and angiogenesis. The method includes the step of administering to a subject (including an animal, especially a mammal, and a human patient) an effective amount of either an FGF2 mutant polypeptide acting as antagonist of FGF2 described above and herein or a nucleic acid comprising a polynucleotide sequence encoding the FGF2 mutant polypeptide. In some embodiments, the polypeptide or nucleic acid is administered orally; or it may be administered topically; or it may be administered intravenously. In some embodiments, the nucleic acid is an expression cassette (such as a circular vector) that contains a promoter operably linked to the polynucleotide coding sequence to direct the expression of the FGF2 mutant polypeptide within recipient cells. In the case of cancer treatment, the patient receiving treatment may already have a vascularized solid tumor or metastases from a primary tumor. In some applications, the method further involves co-administration of an anti-cancer agent, such as an anti-angiogenic agent to the subject. Exemplary anti-angiogenic agents include CB3988, WEB 2086, INF-2α, TNP-470, endostatin, SU 5416, SU 6668, batimistat, angiostatin, and celecoxib. In some embodiments, the subject receiving the FGF2 mutant antagonist is a mammal, such as a human patient.

In a third aspect, the present invention provides a kit for suppressing FGF2-mediated cellular signaling, for example, for suppressing angiogenesis in cancer treatment context. In some embodiments, the kit includes (1) a first composition comprising an FGF2 mutant polypeptide described above and herein that acts as an FGF2 antagonist, or a nucleic acid comprising a polynucleotide sequence encoding the FGF2 mutant polypeptide; and (2) a second composition comprising an anti-inflammatory or anti-tumor agent (e.g., chemotherapeutic agent), such as an anti-angiogenesis agent. Exemplary anti-angiogenic agents include CB3988, WEB 2086, INF-2α, TNP-470, endostatin, SU 5416, SU 6668, batimistat, angiostatin, and celecoxib. In some cases, user instructions for the application of the first and second compositions are included in the kit.

BRIEF DESCRIPTION OF THE DRAWINGS

FIG. 1A) Docking simulation of interaction between FGF2 and integrin αvβ3. Docking simulation was performed as described [11] using the crystal structure of FGF2 (2FGF) and αvβ3 (1LG5). The docking model (docking energy −22.0 kcal/mol) predicts that FGF2 binds to the RGD-binding site of αvβ3 at a high affinity. Several amino acid residues of FGF2 (e.g., Lys at position 125, K125) were chosen for mutagenesis studies. FIG. 1B) Binding of FGF2 mutants to α5β1 in adhesion assays. Binding of FGF2 mutants to α5β1 was tested in adhesion assays using K562 erythroleukemia cells (α5β1+, αvβ3−). K125E and K119E/R120E showed very weak binding. FIG. 1C) Binding of WT FGF2 to soluble αvβ3 in surface plasmon resonance (SPR). Each individual binding curve was fitted on rate and then off rate, $K_d$ for each individual curve was calculated, then averaged out. WT FGF2 bound well to immobilized αvβ3 at $K_d$=7.75×10$^{-8}$ M. which is consistent with docking simulation and previous reports. FIG. 1D) Binding of K125E FGF2 mutant to soluble αvβ3 in SPR. The curves were fitted globally with conformation change model, in which A+B<=>AB ($K_d1$) and then AB<=>AB* ($K_d2$). $K_d1$ is used as the binding $K_d$ to compare with WT's $K_d$. WT K125E bound to immobilized αvβ3 at a low affinity $K_d$=1.1×10$^{-6}$ M. K119E/R120E did not show detectable binding (not shown).

FIG. 3A) ERK1/2 activation. HUVEC cells were stimulated with WT FGF2 (5 ng/ml) or FGF2 mutants (5 ng/ml) for 60 min. Cell lysates were analyzed by western blotting using anti-phosphorylated ERK1/2 and total ERK1/2. FIG. 3B) Cell migration. Lower side of the filter in the Transwell chamber was coated with fibronectin (10 μg/ml). The lower chamber was filled with serum-free medium with WT FGF2 (5 ng/ml), mutants (5 ng/ml) or the mixture of WT FGF2 and mutants (5 and 250 ng/ml, respectively). HUVECs were plated on the filter and incubated for 6 h. Chemotaxed cells were stained and counted from the digital images. Data are shown as means +/−SE of the number of cells per field.

FIG. 4) Serum-starved HUVECs were plated on Matrigel-coated plates, and incubated with WT FGF2 (5 ng/ml), FGF2 mutants (each 5 ng/ml) or the mixture of WT FGF2 (5 ng/ml) and FGF2 mutants (250 ng/ml) for 8 h. The formation of tube-like structures was observed under bright field. Images of representative tube formation are shown. Scale bar=200 μm. FIG. 4B) The number of branching points was counted per field from the images.

FIG. 5A) Isolated rat aortic ring was embedded in collagen gels in DMEM containing FGF2 WT (50 ng/ml) or mutants (each 50 ng/ml), or the mixture of WT FGF2 (50 ng/ml) and mutants (each 2.5 μg/ml) and cultured for 10 days. Representative images of 3 independent experiments are shown. FIG. 5B) The areas of sprouting were counted per field from the images. Scale bar=200 μm. Data is shown as means +/−SE.

FIG. 6A) Hydrogel containing WT FGF2 (100 ng/ml), FGF2 mutants (100 ng/ml) or the mixture of WT FGF2 (100 ng/ml) and excess FGF2 mutants (5 μm/ml) were implanted subcutaneously into the back of rat, respectively. The epidermis, dermis and subcutaneous tissue were removed 2 weeks after implantation and tissue sections were stained for von Willebrand factor. Representative images are shown. FIG. 6B) Three samples were obtained from each condition. The von Willebrand factor positive cells were counted. Data are shown as means +/−SE.

DEFINITIONS

Figure 1A:
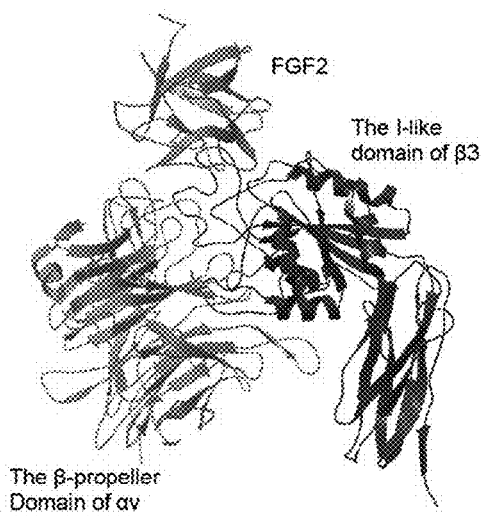
FIGS. 1A-1D. Binding of FGF2 to integrins.

"Inflammation" is a refers to an organism's immune response to irritation, toxic substances, pathogens, or other stimuli. The response can involve innate immune components and/or adaptive immunity. Inflammation is generally characterized as either chronic or acute. Acute inflammation is characterized by redness, pain, heat, swelling, and/or loss of function due to infiltration of plasma proteins and leukocytes to the affected area. Chronic inflammation is characterized by persistent inflammation, tissue destruction, and attempts at repair. Monocytes, macrophages, plasma B cells, and other lymphocytes are recruited to the affected area, and angiogenesis and fibrosis occur, often leading to scar tissue.

An "inflammatory condition" is one characterized by or involving an inflammatory response, as described above. A list of exemplary inflammatory conditions includes: asthma, autoimmune disease, chronic inflammation, chronic prostatitis, glomerulonephritis, hypersensitivities and allergies, skin disorders such as eczema, inflammatory bowel disease, pelvic inflammatory disease, reperfusion injury, rheumatoid arthritis, transplant rejection, and vasculitis.

As used herein, "angiogenesis" refers to a process during which new blood vessels are formed from pre-existing blood vessels. This process involves the migration, growth, and differentiation of endothelial cells, which line the inside wall of blood vessels. While angiogenesis is a normal and vital process in growth and development, as well as in wound healing and in the formation of granulation tissue, it is also a fundamental step in the transition of tumors from a benign state to a malignant one. Anti-angiogenic agents are therefore often used as therapeutics in cancer treatment.

As used herein, "FGF2" refers to a member of the fibroblast growth factor (FGF) family. In this application, an "FGF2 protein" refers to a full-length FGF2 polypeptide sequence, including the human FGF2 (GenBank Accession No. NP_001997.5, encoded by GenBank Accession No. NM_002006.4), its polymorphic variants and species orthologs or homologs. An "FGF2 polynucleotide" refers to a nucleic acid sequence from the gene encoding the FGF2 protein and may include both the coding and non-coding regions. "FGF2 cDNA," "FGF2 mRNA," "FGF2 coding sequence," and their variations refer to a nucleic acid sequence that encodes an FGF2 polypeptide.

"An FGF2 dominant negative mutant" or "an FGF2 mutant" as used herein refers to an FGF2 antagonist compound in the form of a mutated FGF2 or a fragment thereof, which suppresses FGF2-induced cellular signaling by way of its interaction with integrins (such as integrin αvβ3 or α5β1) and FGF receptor (FGFR) in a manner that imposes an inhibitory or disruptive effect on the specific binding among wild-type FGF2, FGFR, and integrin, thus inhibiting downstream events normally triggered by FGF2 signaling, for example, FGF2-mediated ERK1/2 phosphorylation, DNA synthesis, cellular proliferation, and angiogenesis. In an exemplary FGF2 dominant negative mutant, one or more amino acid residues predicted to interact with integrin, e.g., Lys-119, Arg-120, and Lys-125 residues, are mutated, either by deletion or by substitution with a different amino acid (e.g., the K119E/R120E and K125E mutations), resulting in the mutant having decreased or even abolished capability to bind integrin such as αvβ3 or α5β1. These FGF2 dominant negative mutants can be identified based on their deficiency compared to the wild-type FGF2 in decreased integrin binding, as well as in signaling functions (failure to activate ERK1/2 and DNA synthesis for example) in test cells (e.g., NIH3T3 cells). They can also be identified by their capability to suppress FGF2 signaling induced by wild-type FGF2 in test cells such as endothelial cells, in addition to their anti-angiogenic activity, e.g., suppressing tube formation in vitro, sprouting in aorta ring assays ex vivo, or angiogenesis in vivo. An FGF2 dominant negative mutant may be initially generated based on the wild-type FGF2 amino acid sequence (i.e., SEQ ID NO:1) with certain amino acid residue(s) mutated, it may further includes one or more heterologous amino acid sequences (derived from a source other than FGF2 protein) at its N-terminus and/or C-terminus. For example, an FGF2 dominant negative mutant may optionally include one or more additional heterologous amino acid sequence(s) of 1, 2, 3, 4, 5, 6, 7, 8, 9, 10, 11, 12, 13, 14, 15, 16, 17, 18, 19, 20, 25, 30, 35, 40, 45, or up to 50 amino acids at C- and/or N-terminus of the K119E/R120E sequence. Such heterologous peptide sequences can be of a varying nature, for example, any one of the "tags" known and used in the field of recombinant proteins: a peptide tag such as an AviTag, a peptide allowing biotinylation by the enzyme BirA and so the protein can be isolated by streptavidin, a Calmodulin-tag, a peptide bound by the protein calmodulin, a polyglutamate tag, a peptide binding efficiently to anion-exchange resin such as Mono-Q, an E-tag, a peptide recognized by an antibody, a FLAG-tag, a peptide recognized by an antibody, an HA-tag, a peptide recognized by an antibody, a His-tag, 5-10 histidines (SEQ ID NO: 2) bound by a nickel or cobalt chelate, a Myc-tag, a short peptide recognized by an antibody, an S-tag, an SBP-tag, a peptide that specifically binds to streptavidin, a Softag 1 for mammalian expression, a Softag 3 for prokaryotic expression, a Strep-tag, a peptide that binds to streptavidin or the modified streptavidin called streptactin (Strep-tag II), a TC tag, a tetracysteine tag that is recognized by FlAsH and ReAsH biarsenical compounds, a V5 tag, a peptide recognized by an antibody, a VSV-tag, a peptide recognized by an antibody, an Xpress tag; or a covalent peptide tags such as an Isopeptag, a peptide that binds covalently to pilin-C protein, a SpyTag, a peptide that binds covalently to Spy-Catcher protein; or a protein tag such as a BCCP tag (Biotin Carboxyl Carrier Protein), a protein domain biotinylated by BirA enabling recognition by streptavidin, a Glutathione-S-transferase (GST) tag, a protein that binds to immobilized glutathione, a Green fluorescent protein (GFP) tag, a protein that is spontaneously fluorescent and can be bound by nanobodies, a Maltose binding protein (MBP) tag, a protein that binds to amylose agarose, a Nus-tag, a Thioredoxin-tag, an Fc-tag, derived from immunoglobulin Fc domain, allow dimerization and solubilization. A tag that can be used for purification on Protein-A Sepharose; as well as other types of tags such as the Ty tag. Furthermore, the FGF2 dominant negative mutants may also include one or more D-amino acids or include chemical modifications such as glycosylation, PEGylation, crosslinking, and the like.

As used in this application, an "increase" or a "decrease" refers to a detectable positive or negative change in quantity from a comparison control, e.g., an established standard control (such as an average level of ERK1/2 activation or DNA synthesis induced by wild-type FGF2). An increase is a positive change that is typically at least 10%, or at least 20%, or 50%, or 100%, and can be as high as at least 2-fold or at least 5-fold or even 10-fold of the control value. Similarly, a decrease is a negative change that is typically at least 10%, or at least 20%, 30%, or 50%, or even as high as at least 80% or 90% of the control value. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within ±10% of the standard control, or within ±5%, 2%, or even less variation from the standard control.

A composition "consisting essentially of an FGF2 dominant negative mutant" is one that includes an FGF2 mutant that inhibits specific binding among wild-type FGF2, FGFR, and integrin (such as integrin αvβ3 or α5β1) but no other compounds that contribute significantly to the inhibition of the binding. Such compounds may include inactive excipients, e.g., for formulation or stability of a pharmaceutical composition, or active ingredients that do not significantly contribute to the inhibition of FGF2-integrin binding. Exemplary compositions consisting essentially of an FGF2 dominant negative mutant include therapeutics, medicaments, and pharmaceutical compositions.

As used herein, an "effective amount" or a "therapeutically effective amount" means the amount of a compound that, when administered to a subject or patient for treating a disorder, is sufficient to prevent, reduce the frequency of, or alleviate the symptoms of the disorder. The effective amount will vary depending on a variety of the factors, such as a particular compound used, the disease and its severity, the age, weight, and other factors of the subject to be treated. Amelioration of a symptom of a particular condition by administration of a pharmaceutical composition described herein refers to any lessening, whether permanent or temporary, that can be associated with the administration of the pharmaceutical composition. For example, the amount of an FGF2 dominant negative mutant is considered therapeutically effective for treating a condition involving undesired angiogenesis (such as tumor vascularization) when treatment results in eliminated symptoms, delayed onset of symptoms, or reduced frequency or severity of symptoms such as tumor growth, metastasis, etc.

A "subject," or "subject in need of treatment," as used herein, refers to an individual who seeks medical attention due to risk of, or actual sufferance from, a condition involving an undesirable angiogenesis or cancer cell proliferation. The term subject can include both animals, especially mammals, and humans. Subjects or individuals in need of treatment include those that demonstrate symptoms of undesirable angiogenesis and/or tumor cell proliferation or are at risk of later developing these conditions and/or symptoms.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985); and Cassol et al., (1992); Rossolini et al., *Mol. Cell. Probes,* 8:91-98 (1994)). The terms nucleic acid and polynucleotide are used interchangeably with gene, cDNA, and mRNA encoded by a gene.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence. Other elements that may be present in an expression cassette include those that enhance transcription (e.g., enhancers) and terminate transcription (e.g., terminators), as well as those that confer certain binding affinity or antigenicity to the recombinant protein produced from the expression cassette.

The term "heterologous," as used in the context of describing the relative location of two elements, refers to the two elements such as two polynucleotide sequences (e.g., a promoter and a polypeptide-encoding sequence) or polypeptide sequences (e.g., a first amino acid sequence (such as one set forth in SEQ ID NO:1 with mutation or mutations) and a second peptide sequence serving as a fusion partner with the first amino acid sequence) that are not naturally found in the same relative position. Thus, a "heterologous promoter" of a gene refers to a promoter that is not naturally operably linked to that gene. Similarly, a "heterologous polypeptide/amino acid sequence" or "heterologous polynucleotide" to an amino acid sequence or its encoding sequence is one derived from a non-FGF2 origin or derived from FGF2 but not naturally connected to the first FGF2-derived sequence (e.g., one set forth in SEQ ID NO:1) in the same fashion. The fusion of an FGF2-derived amino acid sequence (or its coding sequence) with a heterologous polypeptide (or polynucleotide sequence) does not result in a longer polypeptide or polynucleotide sequence that can be found naturally in FGF2.

DETAILED DESCRIPTION OF THE INVENTION

I. Introduction

It was recently discovered that integrin αvβ3 binds to FGF1, and that the integrin-binding defective FGF1 mutant (Arg-50 to Glu, R50E) is defective in signaling and antagonistic to FGF1 signaling. R50E suppresses angiogenesis and tumor growth, suggesting that R50E has potential as a therapeutic. However, FGF1 is unstable, and R50E had to be expressed in cancer cells for xenograft study, since injected R50E may rapidly disappear from circulation. This study was aimed to determine whether an antagonist can be developed for the more stable FGF2. FGF2 is widely involved in important biological processes such as stem cell proliferation and angiogenesis. Previous studies found that FGF2 bound to αvβ3, and antagonists to αvβ3 suppressed FGF2-induced angiogenesis. Yet it remained unclear how FGF2 interacts with integrins. Here the present inventors describe that substituting Lys-119/Arg-120 and Lys-125 residues in the predicted integrin-binding interface of FGF2 to Glu (e.g., the K119E/R120E and K125E mutations) effectively reduced integrin binding to FGF2. These FGF2 mutants were defective in signaling functions (ERK1/2 activation and DNA synthesis) in NIH3T3 cells. Notably they suppressed FGF2 signaling induced by WT FGF2 in endothelial cells, indicating that these FGF2 mutants are antagonists. The FGF2 mutants effectively suppressed tube formation in vitro, sprouting in aorta ring assays ex vivo, and angiogenesis in vivo. The positions of amino acids critical for integrin binding are different between FGF1 and FGF2, suggesting that they do not interact with integrins in the same manner. The newly developed FGF2 mutants have potential as anti-angiogenic agents and useful tools for studying the role of integrins in FGF2 signaling.

II. Recombinant Expression of Polypeptides

A. General Recombinant Technology

Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The polynucleotide sequence encoding a polypeptide of interest, e.g., an FGF2 dominant negative mutant polypeptide, and synthetic oligonucleotides can be verified after cloning or subcloning using, e.g., the chain termination method for sequencing double-stranded templates of Wallace et al., *Gene* 16: 21-26 (1981).

B. Cloning and Subcloning of a Coding Sequence

The polynucleotide sequences encoding human FGF2 is known as GenBank Accession No. NM_002006.4. The corresponding amino acid sequence is known as GenBank Accession No. NP_001997.5. These polynucleotide sequences may be obtained from a commercial supplier or by amplification methods such as polymerase chain reaction (PCR).

The rapid progress in the studies of human genome has made possible a cloning approach where a human DNA sequence database can be searched for any gene segment that has a certain percentage of sequence homology to a known nucleotide sequence. Any DNA sequence so identified can be subsequently obtained by chemical synthesis and/or PCR technique such as overlap extension method. For a short sequence, completely de novo synthesis may be sufficient; whereas further isolation of full length coding sequence from a human cDNA or genomic library using a synthetic probe may be necessary to obtain a larger gene.

Alternatively, a polynucleotide sequence encoding an FGF2 polypeptide can be isolated from a cDNA or genomic DNA library using standard cloning techniques such as PCR, where homology-based primers can often be derived from a known nucleic acid sequence encoding an integrin polypeptide. This approach is particularly useful for identifying variants, orthologs, or homologs of FGF2. Most commonly used techniques for this purpose are described in standard texts, e.g., Sambrook and Russell, supra.

cDNA libraries suitable for obtaining a coding sequence for a human FGF2 polypeptide may be commercially available or can be constructed. The general methods of isolating mRNA, making cDNA by reverse transcription, ligating cDNA into a recombinant vector, transfecting into a recombinant host for propagation, screening, and cloning are well known (see, e.g., Gubler and Hoffman, *Gene,* 25: 263-269 (1983); Ausubel et al., supra). Upon obtaining an amplified segment of nucleotide sequence by PCR, the segment can be further used as a probe to isolate the full length polynucleotide sequence encoding the gene of interest (e.g., human FGF2) from the cDNA library. A general description of appropriate procedures can be found in Sambrook and Russell, supra. A similar procedure can be followed to obtain a sequence encoding a human FGF2 from a human genomic library, which may be commercially available or can be constructed according to various art-recognized methods. Based on sequence homology, degenerate oligonucleotides can be designed as primer sets and PCR can be performed under suitable conditions (see, e.g., White et al., *PCR Protocols: Current Methods and Applications,* 1993; Griffin and Griffin, *PCR Technology,* CRC Press Inc. 1994) to amplify a segment of nucleotide sequence from a cDNA or genomic library.

Upon acquiring a polynucleotide sequence encoding an FGF2 sequence, the sequence can be modified and then subcloned into a vector, for instance, an expression vector, so that a recombinant polypeptide (e.g., an FGF2 dominant negative mutant polypeptide) can be produced from the resulting construct. Further modifications to the coding sequence, e.g., nucleotide substitutions, may be subsequently made to alter the characteristics of the polypeptide.

C. Modification of a Polynucleotide Coding Sequence

The amino acid sequence of an FGF2 polypeptide may be modified in order to achieve the dominant negative phenotype that inhibits FGF2 cellular signaling, angiogenesis, and cancer cell proliferation, as determined by the in vitro or in vivo methods known in the field as well as described herein. Possible modifications to the amino acid sequence may include conservative substitutions; deletion or addition of one or more amino acid residues (e.g., addition at one terminal of the polypeptide of a tag sequence such as 6× His (SEQ ID NO: 3) to facilitate purification or identification) at either or both of the N- and C-termini.

A variety of mutation-generating protocols are established and described in the art, and can be readily used to modify a polynucleotide sequence encoding an integrin β fragment polypeptide. See, e.g., Zhang et al., *Proc. Natl. Acad. Sci. USA,* 94: 4504-4509 (1997); and Stemmer, *Nature,* 370: 389-391 (1994). The procedures can be used separately or in combination to produce variants of a set of nucleic acids, and hence variants of encoded polypeptides. Kits for mutagenesis, library construction, and other diversity-generating methods are commercially available.

Mutational methods of generating diversity include, for example, site-directed mutagenesis (Botstein and Shortle, *Science,* 229: 1193-1201 (1985)), mutagenesis using uracil-containing templates (Kunkel, *Proc. Natl. Acad. Sci. USA,* 82: 488-492 (1985)), oligonucleotide-directed mutagenesis (Zoller and Smith, *Nucl. Acids Res.,* 10: 6487-6500 (1982)), phosphorothioate-modified DNA mutagenesis (Taylor et al., *Nucl. Acids Res.,* 13: 8749-8764 and 8765-8787 (1985)), and mutagenesis using gapped duplex DNA (Kramer et al., *Nucl. Acids Res.,* 12: 9441-9456 (1984)).

Other possible methods for generating mutations include point mismatch repair (Kramer et al., *Cell*, 38: 879-887 (1984)), mutagenesis using repair-deficient host strains (Carter et al., *Nucl. Acids Res.*, 13: 4431-4443 (1985)), deletion mutagenesis (Eghtedarzadeh and Henikoff, *Nucl. Acids Res.*, 14: 5115 (1986)), restriction-selection and restriction-purification (Wells et al., *Phil. Trans. R. Soc. Lond. A*, 317: 415-423 (1986)), mutagenesis by total gene synthesis (Nambiar et al., *Science*, 223: 1299-1301 (1984)), double-strand break repair (Mandecki, *Proc. Natl. Acad. Sci. USA*, 83: 7177-7181 (1986)), mutagenesis by polynucleotide chain termination methods (U.S. Pat. No. 5,965,408), and error-prone PCR (Leung et al., *Biotechniques*, 1: 11-15 (1989)).

D. Modification of Nucleic Acids for Preferred Codon Usage in a Host Organism

The polynucleotide sequence encoding an FGF2 dominant negative mutant polypeptide can be further altered to coincide with the preferred codon usage of a particular host. For example, the preferred codon usage of one strain of bacterial cells can be used to derive a polynucleotide that encodes an FGF2 mutant and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell.

At the completion of modification, the coding sequences are verified by sequencing and are then subcloned into an appropriate expression vector for recombinant production of the FGF2 dominant negative mutant polypeptides.

E. Chemical Synthesis of Polypeptides

The amino acid sequence of human FGF2 protein has been established (e.g., GenBank Accession No. NP_001997.5). Polypeptides of known sequences, especially those of relatively short length such as FGF2 amino acid sequence set forth in SEQ ID NO:1, may be synthesized by solid-phase peptide synthesis methods using procedures similar to those described by Merrifield et al., *J. Am. Chem. Soc.*, 85:2149-2156 (1963); Barany and Merrifield, *Solid-Phase Peptide Synthesis, in The Peptides: Analysis, Synthesis, Biology* Gross and Meienhofer (eds.), Academic Press, N.Y., vol. 2, pp. 3-284 (1980); and Stewart et al., *Solid Phase Peptide Synthesis* 2nd ed., Pierce Chem. Co., Rockford, Ill. (1984). During synthesis, N-α-protected amino acids having protected side chains are added stepwise to a growing polypeptide chain linked by its C-terminal and to a solid support, i.e., polystyrene beads. The peptides are synthesized by linking an amino group of an N-α-deprotected amino acid to an α-carboxy group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc, which is acid labile, and Fmoc, which is base labile.

Materials suitable for use as the solid support are well known to those of skill in the art and include, but are not limited to, the following: halomethyl resins, such as chloromethyl resin or bromomethyl resin; hydroxymethyl resins; phenol resins, such as 4-(α[2,4-dimethoxyphenyl]-Fmoc-aminomethyl)phenoxy resin; tert-alkyloxycarbonyl-hydrazidated resins, and the like. Such resins are commercially available and their methods of preparation are known by those of ordinary skill in the art.

Briefly, the C-terminal N-α-protected amino acid is first attached to the solid support. The N-α-protecting group is then removed. The deprotected α-amino group is coupled to the activated α-carboxylate group of the next N-α-protected amino acid. The process is repeated until the desired peptide is synthesized. The resulting peptides are then cleaved from the insoluble polymer support and the amino acid side chains deprotected. Longer peptides can be derived by condensation of protected peptide fragments. Details of appropriate chemistries, resins, protecting groups, protected amino acids and reagents are well known in the art and so are not discussed in detail herein (See, Atherton et al., *Solid Phase Peptide Synthesis: A Practical Approach*, IRL Press (1989), and Bodanszky, *Peptide Chemistry, A Practical Textbook*, 2nd Ed., Springer-Verlag (1993)).

III. Expression and Purification of Recombinant Polypeptides

Following verification of the coding sequence, a polypeptide of interest (e.g., an FGF2 dominant negative mutant polypeptide) can be produced using routine techniques in the field of recombinant genetics, relying on the polynucleotide sequences encoding the polypeptide disclosed herein.

A. Expression Systems

To obtain high level expression of a nucleic acid encoding a polypeptide of interest, one typically subclones the polynucleotide coding sequence into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing recombinant polypeptides are available in, e.g., *E. coli, Bacillus* sp., *Salmonella*, and *Caulobacter*. Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of the desired polypeptide in host cells. A typical expression cassette thus contains a promoter operably linked to the nucleic acid sequence encoding the polypeptide and signals required for efficient polyadenylation of the transcript, ribosome binding sites, and translation termination. The nucleic acid sequence encoding the desired polypeptide is typically linked to a cleavable signal peptide sequence to promote secretion of the recombinant polypeptide by the transformed cell. Such signal peptides include, among others, the signal peptides from tissue plasminogen activator, insulin, and neuron growth factor, and juvenile hormone esterase of *Heliothis virescens*. If, however, a recombinant polypeptide is intended to be expressed on the host cell surface, an appropriate anchoring sequence is used in concert with the coding sequence. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the desired polypeptide under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary. Similar to antibiotic resistance selection markers, metabolic selection markers based on known metabolic pathways may also be used as a means for selecting transformed host cells.

When periplasmic expression of a recombinant polypeptide is desired, the expression vector further comprises a sequence encoding a secretion signal, such as the *E. coli* OppA (Periplasmic Oligopeptide Binding Protein) secretion signal or a modified version thereof, which is directly connected to 5' of the coding sequence of the protein to be expressed. This signal sequence directs the recombinant protein produced in cytoplasm through the cell membrane into the periplasmic space. The expression vector may further comprise a coding sequence for signal peptidase 1, which is capable of enzymatically cleaving the signal sequence when the recombinant protein is entering the periplasmic space. More detailed description for periplasmic production of a recombinant protein can be found in, e.g., Gray et al., *Gene* 39: 247-254 (1985), U.S. Pat. Nos. 6,160,089 and 6,436,674.

As discussed above, a person skilled in the art will recognize that various conservative substitutions can be made to a protein or its coding sequence while still retaining the biological activity of the protein. Moreover, modifications of a polynucleotide coding sequence may also be made to accommodate preferred codon usage in a particular expression host without altering the resulting amino acid sequence.

B. Transfection Methods

Standard transfection methods are used to produce bacterial, mammalian, yeast, insect, or plant cell lines that express large quantities of a recombinant polypeptide, which are then purified using standard techniques (see, e.g., Colley et al., *J. Biol. Chem.* 264: 17619-17622 (1989); Guide to Protein Purification, in *Methods in Enzymology*, vol. 182 (Deutscher, ed., 1990)). Transformation of eukaryotic and prokaryotic cells are performed according to standard techniques (see, e.g., Morrison, *J. Bact.* 132: 349-351 (1977); Clark-Curtiss & Curtiss, *Methods in Enzymology* 101: 347-362 (Wu et al., eds, 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well-known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the recombinant polypeptide.

C. Purification of Recombinantly Produced Polypeptides

Once the expression of a recombinant polypeptide in transfected host cells is confirmed, e.g., by an immunological assay, the host cells are then cultured in an appropriate scale for the purpose of purifying the recombinant polypeptide.

1. Purification of Recombinantly Produced Polypeptide from Bacteria

When desired polypeptides are produced recombinantly by transformed bacteria in large amounts, typically after promoter induction, although expression can be constitutive, the polypeptides may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 µg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques. For further description of purifying recombinant polypeptides from bacterial inclusion body, see, e.g., Patra et al., *Protein Expression and Purification* 18: 182-190 (2000).

Alternatively, it is possible to purify recombinant polypeptides from bacterial periplasm. Where the recombinant protein is exported into the periplasm of the bacteria, the periplasmic fraction of the bacteria can be isolated by cold osmotic shock in addition to other methods known to those of skill in the art (see e.g., Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

2. Standard Protein Separation Techniques for Purification

When a recombinant polypeptide is expressed in host cells in a soluble form, its purification can follow the standard protein purification procedure described below. This standard purification procedure is also suitable for purifying polypeptides obtained from chemical synthesis (e.g., an integrin β fragment).

i. Solubility Fractionation

Often as an initial step, and if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

ii. Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of a protein of interest, e.g., an integrin β fragment polypeptide. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

iii. Column Chromatography

The proteins of interest (such as an FGF2 dominant negative mutant polypeptide) can also be separated from other proteins on the basis of their size, net surface charge, hydrophobicity, or affinity for ligands. In addition, antibodies raised against an FGF2 mutant can be conjugated to column matrices and the corresponding polypeptide immunopurified. All of these methods are well known in the art.

It will be apparent to one of skill that chromatographic techniques can be performed at any scale and using equipment from many different manufacturers (e.g., Pharmacia Biotech).

IV. Conditions Involving Inflammatory Responses, Cell Proliferation, and Angiogenesis Identification and diagnosis of conditions involving inflammation or undesirable cell proliferation and angiogenesis, as well as methods of monitoring the effectiveness of a therapeutic regimen as described herein, are included in the present invention. As explained above, inflammation is generally characterized by redness, swelling, pain, and occasional loss of function. However, symptoms vary among tissues, so that some inflammatory conditions are not easily detectable (e.g., atherosclerosis). Undesirable cell proliferation, on the other hand, is often determined by way of detecting a benign or malignant growth, including an abnormal expansion of a particular cell or tissue type, such as various types of tumors and cancers. Angiogenesis involves the formation of new blood vessels from the existing old vessels, a biological process critical for wound healing and tumorigenesis.

Although the inflammatory response can play a role in the healing process by destroying, diluting, and isolating injurious agents and stimulating repair of the affected tissue, inflammatory responses can also be harmful. For example, inflammation results in leakage of plasma from the blood vessels. Although this leakage can have beneficial effects, it causes pain and when uncontrolled can lead to loss of function and death (such as adult respiratory distress syndrome). Anaphylactic shock, arthritis, and gout are among the conditions that are characterized by uncontrolled or inappropriate inflammation.

On a cellular level, an inflammatory response is typically initiated by endothelial cells producing molecules that attract and detain inflammatory cells (e.g., myeloid cells such as neutrophils, eosinophils, and basophils) at the site of injury or irritation. The inflammatory cells then are transported through the endothelial barrier into the surrounding tissue. The result is accumulation of inflammatory cells, in particular neutrophils. Such accumulation is easily detectable by one of skill.

Adaptive immune cells (T and B cells) are often involved in inflammatory conditions. These cells release cytokines and antibodies in response to the source of the irritation. Thus, an inflammatory response can also be detected by detecting a change in the level of inflammatory cytokines, e.g., in a localized region of irritation or in the serum or plasma of an individual. It will be appreciated by those of skill in the art that each of these symptoms can be detected in an individual for the purposes of diagnosis. Further, a subject undergoing therapy for an inflammatory condition can be monitored, for instance, by detecting any changes in severity of the symptoms. Such inflammatory conditions include rheumatoid arthritis, Alzheimer's disease, multiple sclerosis, and atherosclerosis.

Inappropriate or uncontrolled cellular proliferation is the hallmark of malignant tumor or cancer. For cancer cells, especially those in a solid mass, to continue growth, the formation of new blood vessels or angiogenesis is of critical importance. Thus, the first and foremost important conditions an anti-angiogenic agent is useful for are cancers of various types.

V. Pharmaceutical Compositions and Administration

The present invention also provides pharmaceutical compositions comprising an effective amount of an FGF2 dominant negative mutant polypeptide for inhibiting a pro-inflammatory signal, a pro-proliferation signal, or a pro-angiogenesis signal, therefore useful in both prophylactic and therapeutic applications designed for various diseases and conditions involving undesired inflammation, cell proliferation, and/or angiogenesis. Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985). For a brief review of methods for drug delivery, see, Langer, *Science* 249: 1527-1533 (1990).

The pharmaceutical compositions of the present invention can be administered by various routes, e.g., oral, subcutaneous, transdermal, intramuscular, intravenous, or intraperitoneal. The routes of administering the pharmaceutical compositions include systemic or local delivery to a subject suffering from a condition exacerbated by inflammation at daily doses of about 0.01-5000 mg, preferably 5-500 mg, of an FGF2 mutant polypeptide for a 70 kg adult human per day. The appropriate dose may be administered in a single daily dose or as divided doses presented at appropriate intervals, for example as two, three, four, or more subdoses per day.

For preparing pharmaceutical compositions containing an FGF2 mutant polypeptide, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., an FGF2 mutant polypeptide. In tablets, the active ingredient (the mutant polypeptide) is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active compound of an FGF2 mutant polypeptide with encapsulating material as a carrier providing a capsule in which the mutant (with or without other carriers) is surrounded by the carrier, such that the carrier is thus in association with the compound. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., an FGF2 mutant polypeptide) or sterile solutions of the active component in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., an FGF2 mutant polypeptide) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9, and most preferably from 7 to 8.

The pharmaceutical compositions containing the FGF2 mutant can be administered for prophylactic and/or therapeutic treatments. In therapeutic applications, compositions are administered to a patient already suffering from a condition that may be exacerbated by an undesirable inflammatory reaction/cell proliferation/angiogenesis in an amount sufficient to prevent, cure, reverse, or at least partially slow or arrest the symptoms of the condition and its complications. An amount adequate to accomplish this is defined as a "therapeutically effective dose." Amounts effective for this use will depend on the severity of the disease or condition and the weight and general state of the patient, but generally range from about 0.1 mg to about 2,000 mg of the mutant polypeptide per day for a 70 kg patient, with dosages of from about 5 mg to about 500 mg of the mutant polypeptide per day for a 70 kg patient being more commonly used.

In prophylactic applications, pharmaceutical compositions containing an FGF2 mutant polypeptide are administered to a patient susceptible to or otherwise at risk of developing a disease or condition involving an undesirable inflammatory response, cell proliferation, and/or angiogenesis in an amount sufficient to delay or prevent the onset of the symptoms. Such an amount is defined to be a "prophylactically effective dose." In this use, the precise amounts of the inhibitor again depend on the patient's state of health and weight, but generally range from about 0.1 mg to about 2,000 mg of the mutant polypeptide for a 70 kg patient per day, more commonly from about 5 mg to about 500 mg for a 70 kg patient per day.

Single or multiple administrations of the compositions can be carried out with dose levels and pattern being selected by the treating physician. In any event, the pharmaceutical formulations should provide a quantity of a compound sufficient to effectively inhibit the undesirable inflammatory response/cellular proliferation/angiogenesis mediated by FGF2 signaling in the patient, either therapeutically or prophylactically.

VI. Therapeutic Applications Using Nucleic Acids

A variety of inflammatory conditions or undesirable cell proliferation/angiogenesis can be treated by therapeutic approaches that involve introducing into a cell a nucleic acid encoding an FGF2 dominant negative mutant polypeptide (e.g., K119E/R120E or K125E) such that the expression of the mutant leads to reduced or abolished FGF2 signaling in the cell. Those amenable to treatment by this approach include a broad spectrum of conditions involving undesirable inflammation, cell proliferation, and/or angiogenesis. For discussions on the application of gene therapy towards the treatment of genetic as well as acquired diseases, see, Miller Nature 357:455-460 (1992); and Mulligan Science 260:926-932 (1993).

A. Vectors for Nucleic Acid Delivery

For delivery to a cell or organism, an inhibitory nucleic acid of the invention can be incorporated into a vector. Examples of vectors used for such purposes include expression plasmids capable of directing the expression of the FGF2 mutants in the target cell. In other instances, the vector is a viral vector system wherein the polynucleotide is incorporated into a viral genome that is capable of transfecting the target cell. In a preferred embodiment, the inhibitory nucleic acid can be operably linked to expression and control sequences that can direct transcription of sequence in the desired target host cells. Thus, one can achieve reduced FGF2 signaling under appropriate conditions in the target cell.

B. Gene Delivery Systems

As used herein, "gene delivery system" refers to any means for the delivery of an inhibitory nucleic acid of the invention to a target cell. Viral vector systems useful in the introduction and expression of an inhibitory nucleic acid include, for example, naturally occurring or recombinant viral vector systems. Depending upon the particular application, suitable viral vectors include replication competent, replication deficient, and conditionally replicating viral vectors. For example, viral vectors can be derived from the genome of human or bovine adenoviruses, vaccinia virus, herpes virus, adeno-associated virus, minute virus of mice (MVM), HIV, sindbis virus, and retroviruses (including but not limited to Rous sarcoma virus), and MoMLV. Typically, the inhibitory nucleic acid is inserted into such vectors to allow packaging of the gene construct, typically with accompanying viral DNA, followed by infection of a sensitive host cell and expression of the gene of interest.

Similarly, viral envelopes used for packaging gene constructs that include the inhibitory nucleic acid can be modified by the addition of receptor ligands or antibodies specific for a receptor to permit receptor-mediated endocytosis into specific cells (see, e.g., WO 93/20221, WO 93/14188, and WO 94/06923).

Retroviral vectors may also be useful for introducing the inhibitory nucleic acid of the invention into target cells or organisms. Retroviral vectors are produced by genetically manipulating retroviruses. The viral genome of retroviruses is RNA. Upon infection, this genomic RNA is reverse transcribed into a DNA copy which is integrated into the chromosomal DNA of transduced cells with a high degree of stability and efficiency. The integrated DNA copy is referred to as a provirus and is inherited by daughter cells as is any other gene. The wild type retroviral genome and the proviral DNA have three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site) (see, Mulligan, In: Experimental Manipulation of Gene Expression, Inouye (ed), 155-173 (1983); Mann et al., Cell 33:153-159 (1983); Cone and Mulligan, Proceedings of the National Academy of Sciences, U.S.A., 81:6349-6353 (1984)).

The design of retroviral vectors is well known to those of ordinary skill in the art. In brief, if the sequences necessary for encapsidation (or packaging of retroviral RNA into infectious virions) are missing from the viral genome, the result is a cis acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including, e.g., European Patent Application EPA 0 178 220; U.S. Pat. No. 4,405,712, Gilboa Biotechniques 4:504-512 (1986); Mann et al., Cell 33:153-159 (1983); Cone and Mulligan Proc. Natl. Acad. Sci. USA 81:6349-6353 (1984); Eglitis et al. Biotechniques 6:608-614 (1988); Miller et al. Biotechniques 7:981-990 (1989); Miller (1992) supra; Mulligan (1993), supra; and WO 92/07943.

The retroviral vector particles are prepared by recombinantly inserting the desired inhibitory nucleic acid sequence into a retrovirus vector and packaging the vector with retroviral capsid proteins by use of a packaging cell line. The resultant retroviral vector particle is incapable of replication in the host cell but is capable of integrating into the host cell genome as a proviral sequence containing the desired nucleotide sequence. As a result, the patient is capable of producing, for example, the inhibitory nucleic acid, thus eliminating or reducing unwanted inflammatory conditions.

Packaging cell lines that are used to prepare the retroviral vector particles are typically recombinant mammalian tissue culture cell lines that produce the necessary viral structural proteins required for packaging, but which are incapable of producing infectious virions. The defective retroviral vectors that are used, on the other hand, lack these structural genes but encode the remaining proteins necessary for packaging. To prepare a packaging cell line, one can construct an infectious clone of a desired retrovirus in which the packaging site has been deleted. Cells comprising this construct will express all structural viral proteins, but the introduced DNA will be incapable of being packaged. Alternatively, packaging cell lines can be produced by transforming a cell line with one or more expression plasmids encoding the appropriate core and envelope proteins. In these cells, the gag, pol, and env genes can be derived from the same or different retroviruses.

A number of packaging cell lines suitable for the present invention are also available in the prior art. Examples of these cell lines include Crip, GPE86, PA317 and PG13 (see Miller et al., *J. Virol.* 65:2220-2224 (1991)). Examples of other packaging cell lines are described in Cone and Mulligan *Proceedings of the National Academy of Sciences, USA,* 81:6349-6353 (1984); Danos and Mulligan *Proceedings of the National Academy of Sciences, USA,* 85:6460-6464 (1988); Eglitis et al. (1988), supra; and Miller (1990), supra.

C. Pharmaceutical Formulations

When used for pharmaceutical purposes, the inhibitory nucleic acid is generally formulated in a suitable buffer, which can be any pharmaceutically acceptable buffer, such as phosphate buffered saline or sodium phosphate/sodium sulfate, Tris buffer, glycine buffer, sterile water, and other buffers known to the ordinarily skilled artisan such as those described by Good et al. *Biochemistry* 5:467 (1966).

The compositions can further include a stabilizer, an enhancer, and/or other pharmaceutically acceptable carriers or vehicles. A pharmaceutically acceptable carrier can contain a physiologically acceptable compound that acts, for example, to stabilize the inhibitory nucleic acids of the invention and any associated vector. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. Examples of carriers, stabilizers or adjuvants can be found in *Remington's Pharmaceutical Sciences,* Mack Publishing Company, Philadelphia, Pa., 17th ed. (1985).

D. Administration of Formulations

The formulations containing an inhibitory nucleic acid can be delivered to any tissue or organ using any delivery method known to the ordinarily skilled artisan. In some embodiments of the invention, the nucleic acid is formulated in mucosal, topical, and/or buccal formulations, particularly mucoadhesive gel and topical gel formulations. Exemplary permeation enhancing compositions, polymer matrices, and mucoadhesive gel preparations for transdermal delivery are disclosed in U.S. Pat. No. 5,346,701.

The formulations containing the inhibitory nucleic acid are typically administered to a cell. The cell can be provided as part of a tissue or as an isolated cell, such as in tissue culture. The cell can be provided in vivo, ex vivo, or in vitro.

The formulations can be introduced into the tissue of interest in vivo or ex vivo by a variety of methods. In some embodiments of the invention, the inhibitory nucleic acid is introduced into cells by such methods as microinjection, calcium phosphate precipitation, liposome fusion, ultrasound, electroporation, or biolistics. In further embodiments, the nucleic acid is taken up directly by the tissue of interest.

In some embodiments of the invention, the inhibitory nucleic acid is administered ex vivo to cells or tissues explanted from a patient, then returned to the patient. Examples of ex vivo administration of therapeutic gene constructs include Nolta et al., *Proc Natl. Acad. Sci. USA* 93 (6):2414-9 (1996); Koc et al., *Seminars in Oncology* 23 (1):46-65 (1996); Raper et al., *Annals of Surgery* 223 (2):116-26 (1996); Dalesandro et al., *J. Thorac. Cardi. Surg.,* 11 (2):416-22 (1996); and Makarov et al., *Proc. Natl. Acad. Sci. USA* 93 (1):402-6 (1996).

Effective dosage of the formulations will vary depending on many different factors, including means of administration, target site, physiological state of the patient, and other medicines administered. Thus, treatment dosages will need to be titrated to optimize safety and efficacy. In determining the effective amount of the vector to be administered, the physician should evaluate the particular nucleic acid used, the disease state being diagnosed; the age, weight, and overall condition of the patient, circulating plasma levels, vector toxicities, progression of the disease, and the production of anti-vector antibodies. The size of the dose also will be determined by the existence, nature, and extent of any adverse side-effects that accompany the administration of a particular vector. To practice the present invention, doses ranging from about 10 ng-1 g, 100 ng-100 mg, 1 μg-10 mg, or 30-300 μg inhibitory nucleic acid per patient are typical. Doses generally range between about 0.01 and about 50 mg per kilogram of body weight, preferably between about 0.1 and about 5 mg/kg of body weight or about $10^8$-$10^{10}$ or $10^{12}$ viral particles per injection. In general, the dose equivalent of a naked nucleic acid from a vector is from about 1 μg-100 μg for a typical 70 kg patient, and doses of vectors which include a retroviral particle are calculated to yield an equivalent amount of an inhibitory nucleic acid.

VII. Kits

The invention also provides kits for suppressing FGF2-induced cellular signaling or treating a condition involving undesirable inflammatory responses and/or angiogenesis including cancer cell proliferation by inhibiting the specific binding between FGF2 and integrin according to the method of the present invention. The kits typically include a first container that contains a pharmaceutical composition having an effective amount of an FGF2 dominant negative mutant, optionally with a second container containing an anti-cancer agent, such as another anti-angiogenic agent, such as bevacizumab (Avastin), itraconazole, carboxyamidotriazole, TNP-470, CM101, IFN-α, IL-12, platelet factor-4, suramin, SU5416, thrombospondin, VEGFR antagonists, angiostatin, endostatin, 2-methoxyestradiol, tecogalan, tetrathiomolybdate, thalidomide, prolactin, αVβ3 inhibitors, linomide, ramucirumab, tasquinimod, ranibizumab, sorafenib(Nexavar®), sunitinib (Sutent®), pazopanib (Votrient®), and everolimus (Afinitor®). In some cases, the kits will also include informational material containing instructions on how to dispense the pharmaceutical composition, including description of the type of patients who may be treated (e.g., a person suffering from cancer or at risk of developing secondary metastasis), the schedule (e.g., dose and frequency of administration) and route of administration, and the like.

EXAMPLES

The following examples are provided by way of illustration only and not by way of limitation. Those of skill in the art will readily recognize a variety of non-critical parameters that could be changed or modified to yield essentially the same or similar results.

Example 1

Introduction

The fibroblast growth factor (FGF) family consists of 22 related polypeptides that are expressed in almost all tissues and are multifunctional. Some FGFs, like FGF1 and FGF2, have potent angiogenic activity and are implicated as promoters of angiogenesis, the formation of new blood vessels, in cancer and chronic inflammatory diseases [1-3]. FGFs also increase the motility and invasiveness of a variety of cell types. The biological effects of FGFs are mediated by four structurally related receptor tyrosine kinases: Fibroblast growth factor receptor-1 (FGFR1), FGFR2, FGFR3, and FGFR4. The binding of FGF to its receptor results in receptor dimerization and subsequent autophosphorylation of specific tyrosine residues within the intracellular domain. This leads to the activation of intracellular signaling cascades. Integrins are a family of cell adhesion receptors that recognize extracellular matrix (ECM) ligands and cell surface ligands [4]. Integrins are transmembrane α-β heterodimers, and at least 18 α and 8 β subunits are known [5]. Integrins are involved in signal transduction upon ligand binding and their functions are in turn regulated by signals from within the cell [5]. Previous studies found that antagonists to integrin αvβ3 suppressed angiogenesis induced by FGF2 [6], suggesting that this integrin is involved in FGF2 signaling (FGF-integrin crosstalk). Crosstalk between integrins and FGFs are an important signaling mechanism during normal development and pathological processes [7]. Current models of integrin-growth factor crosstalk propose that integrins contribute to growth factor signaling through interaction of integrins with the ECM [8-10]. It was previously reported that FGF1 specifically binds to the classical RGD-binding site of integrin αvβ3 (KD about 1 μM) using docking simulation and mutagenesis [11, 12]. The integrin binding site in FGF1 is distinct from the FGFR-binding site. An FGF1 mutant (the Arg-50 to Glu mutant, R50E), which is defective in integrin binding but still binds to heparin and FGFR1, is defective in inducing DNA synthesis, cell proliferation, cell migration, and chemotaxis, suggesting that the direct integrin binding to FGF1 is critical for FGF1 signaling [13]. The present inventors proposed a model in which integrin and FGFR bind to FGF1 simultaneously and make a ternary complex on the cell surface. They discovered that R50E is a dominant-negative antagonist of FGF1. R50E suppressed DNA synthesis and cell proliferation induced by WT FGF1 [13], and suppressed angiogenesis in vitro and in vivo [14]. Using cancer cells that stably express WT FGF1 or R50E, they showed that WT FGF1 markedly enhanced tumor growth and R50E suppressed it [14]. Therefore, the R50E mutant of FGF1 has potential as a therapeutic (FGF1 decoy). FGF1 is, however, thermodynamically unstable ($T_m$=40° C.). R50E had to be expressed in cancer cells to demonstrate its antagonistic effects on tumor growth and angiogenesis since it is believed that R50E is quickly removed from circulation if R50E is systematically injected into mice in xenograft experiments [14]. FGF2 is thermodynamically more stable ($T_m$=59° C.) and has a longer half-life in circulation than FGF1. FGF2 is widely involved in important biological processes such as stem cell proliferation and angiogenesis partly due to its stability [1]. It has been reported that integrin αvβ3 binds to immobilized FGF2 and promote endothelial cell adhesion and spreading [15]. Also, anti-αvβ3 monoclonal and polyclonal antibodies specifically inhibit cell proliferation and up regulation of the urokinase-type plasminogen activator induced by soluble FGF2 in GM 7373 cells grown on tissue culture plastic [15]. It is unclear, however, how FGF2 interacts with integrins. The goal of this study is to determine how integrins bind to FGF2 and to determine if integrin-binding defective FGF2 is dominant-negative as in the case of FGF1. In the present study the present inventors developed FGF2 mutants that are defective in integrin binding and found that such FGF2 mutants act as antagonists of FGF2 signaling (FGF2 decoys). Notably, these FGF2 mutants effectively suppressed angiogenesis. Such FGF2 mutants can serve as cancer therapeutics by virtue of their anti-angiogenic activity.

Materials and Methods

Materials: All chemicals were purchased from Thermo Fisher Scientific, Sigma (St. Louis, Mo.), or Nacalai tesque (Kyoto, Japan) unless otherwise stated. NIH3T3 embryonic mouse fibroblasts were obtained from American Type Culture Collection (ATCC) and were maintained in DMEM supplemented with 10% FCS and antibiotics. Human umbilical endothelial cells (HUVEC) were purchased from Sanko-junyaku (Tokyo, Japan) and were routinely cultured in EGM-2 Bullet kit (Lonza Basel, Switzerland) supplemented with 2% FCS. K562 Erythroleukemia cells and K562 cells that express recombinant αvβ3 were described before [11]. Recombinant soluble αvβ3 was synthesized as described [16].

Synthesis of FGF2: A fragment of cDNA encoding human FGF2 (SEQ ID NO:1, PALPEDGGSGAFPPGHFKDPKR-LYCKNGGFFLRIHPDGRVDGVREKSDPHIKLQLQA EERGVVSIKGVCANRYLAMKEDGRLLASKCVT-DECFFFERLESNNYNTYRSRKYTS WYVALKRTGQYKLGSKTGPGQKAILFLPMSAKS) was amplified by PCR using full-length human FGF2 cDNA as a template and subcloned into the BamHI/EcoRI site of PET28a+. Protein was synthesized in *E. coli* BL21 and purified by Ni-NTA affinity chromatography. WT and mutant FGF2 migrated as single bands in SDS-PAGE (data not shown).

Docking Simulation: Docking simulation of interaction between FGF2 (2FGF.pdb) and integrin αvβ3 (1L5G.pdb, open-headpiece form) was performed using AutoDock 3.05 as described [11]. Cations were not present in αvβ3 during docking simulation [11, 16]. The ligand is presently compiled to a maximum size of 1024 atoms. Atomic solvation parameters and fractional volumes were assigned to the protein atoms by using the AddSol utility, and grid maps were calculated by using AutoGrid utility in AutoDock 3.05. A grid map with 127×127×127 points and a grid point spacing of 0.603 Å included the headpiece of αvβ3 (residues 1-438 of αv and residues 55-432 of β3). Kollman "united-atom" charges were used. AutoDock 3.05 uses a Lamarckian genetic algorithm (LGA) that couples a typical Darwinian genetic algorithm for global searching with the Solis and Wets algorithm for local searching. The LGA parameters were defined as follows: the initial population of random individuals had a size of 50 individuals; each docking was terminated with a maximum number of $1\times10^6$ energy evaluations or a maximum number of 27,000 generations, whichever came first; mutation and crossover rates were set at 0.02 and 0.80, respectively. An elitism value of 1 was applied, which ensured that the top ranked individual in the population always survived into the next generation. A maximum of 300 iterations per local search was used. The probability of performing a local search on an individual was 0.06, whereas the maximum number of consecutive successes or failures before doubling or halving the search step size was 4.

Surface plasmon resonance (SPR) study: SPR was performed as previously described [11]. Briefly, soluble αvβ3 was immobilized on the CM5 sensor chip using a standard amine coupling procedure [17]. The WT and mutant FGF2 were individually 2-fold serially diluted from 2 μM in HBS-P buffer (0.01 M Hepes, pH 7.4, 0.15 M NaCl, and 0.0005% of surfactant P20) with 1 mM of $Mn^{2+}$. Samples were injected at 50 μl/min for 1.8 min. The HBS-P buffer with 1 mM of $Mn^{2+}$ was then injected at 50 μl/min for 3 min to allow the bound FGF2s to dissociate from the integrin.

BrdU Incorporation Assay: DNA synthesis was measured by the cell proliferation ELISA BrdU kit (Roche Diagnostics, Basel, Switzerland). NIH3T3 cells were starved for 16 h. Cells were stimulated with either WT FGF2 or mutants on 96 well plate for 24 h and concomitantly BrdU solution was added to the culture. The mixture of WT FGF2 (5 ng/ml) and each mutant (250 ng/ml) were also tested. The amplitude of absorbance at 450 nm is proportional to the BrdU incorporation into the cells.

Cell Migration Assay: Cell migration assay was performed as previously described [14]. Briefly, the membrane was placed into a 24-well cell culture plate, and the lower portion of the plate was filled with serum-free EBM-2 medium containing 5 ng/ml WT FGF2, K119E/R120E, or K125E. The mixture of WT FGF2 (5 ng/ml) and individual mutants (5 ng/ml), or the mixture were also tested. Starved HUVEC cells ($6 \times 10^4$ cells/filter) were plated on the filter and incubated at 37° C. for 6 h. Chemotaxed cells were stained for visualization and counted.

Endothelial Cell Tube Formation Assay: Endothelial cell tube formation assay was performed as described [14]. In brief, serum-starved HUVECs were plated in wells ($3 \times 10^4$ cells/well) of 48 well plates coated with 150 μl Matrigel (BD Biosciences, San Jose, Calif.). The medium contains 5 ng/ml WT FGF2, or the mixture of WT FGF2 (5 ng/ml), individual mutants (5 ng/ml), or the mixture (5 and 250 ng/ml, respectively). Cells were incubated for 6 h at 37° C. The Number of vessel branch points of tube per field was counted from the digital images.

Ex Vivo Aorta Ring Assay: Thoracic aortae were isolated from 8 week-old rats and used for aorta ring assay as described previously [14]. Briefly, aortic segments were embedded into Type I collagen (Nitta Gelatin, Osaka, Japan) that contains WT FGF2 (50 ng/ml), individual mutants (50 ng/ml), or the mixture (50 and 2500 ng/ml, respectively). Aortic ring sprouts on days 10 were photographed.

In vivo Angiogenesis Assay: Hydrogels (MedGEL, Tokyo, Japan) were immersed in WT FGF2 (100 ng/ml), FGF2 mutant (100 ng/ml) or the mixture (100 ng and 5 μg/ml, respectively) and were implanted subcutaneously into the back of 10 weeks-old rats. The epidermis, dermis and subcutaneous tissue were removed 2 weeks after implantation and tissue sections were stained for von Willebrand factor using antibody specific to von Willebrand factor (Abcam, Tokyo, Japan) to detect blood vessel. The number of blood vessels was counted under a light microscope.

Other Methods: Mutagenesis of FGF2 was performed as previously described [11]. Cell adhesion assays [18] and binding assays [19] were performed as described. Statistical significance was tested in Prism 6 (GraphPad Software) using analysis of variance (ANOVA) and Tukey's multiple-comparison test to control the global type I error.

Results

Identification of Amino Acid Residues That are Critical for Integrin Binding

Figure 1B:
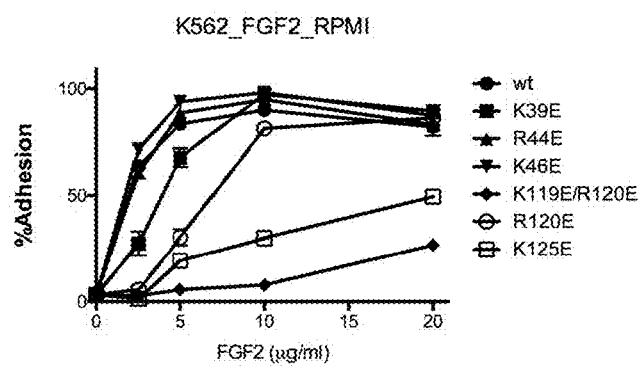
Figure 1C:
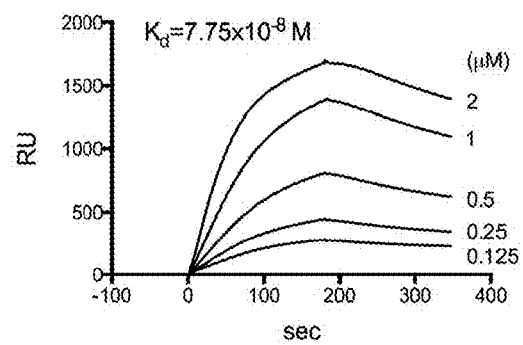
Figure 1D:
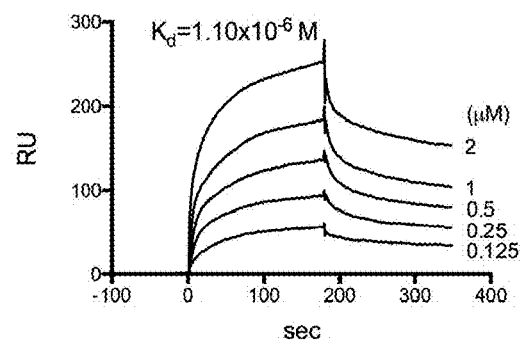

To identify how integrin αvβ3 and FGF2 interact, docking simulation of interaction between αvβ3 (PDB code 1L5G) and FGF2 (PDB code 2FGF) was performed using autodock3 (FIG. 1a). The simulation predicted that FGF2 binds to the classical RGD-binding site of αvβ3 with high affinity (docking energy −22 kcal/mol). When the FGFR1-FGF2 complex (1FQ9) is superposed to the αvβ3-FGF2 complex, there was little or no steric hindrance, suggesting that FGF2 can simultaneously bind to FGFR1 and αvβ3. The predicted integrin-binding interface overlaps with the heparin-binding site (residues 119-128, KRTGQYKLGS (SEQ ID NO: 4)). To generate FGF2 mutants that are defective in integrin binding, mutations were introduced into several amino acid residues (K39, R44, K46, K119/R120, and K125 to E) within the predicted integrin-binding interface of FGF2 (Table 1). It was studied if the FGF2 mutants support adhesion of K562 cells that express recombinant integrin αvβ3 (αvβ3-K562 cells) and parent K562 cells. K562 cells that are deficient in proteoglycans were chosen because FGF2 strongly binds to cell surface proteoglycans (e.g., on CHO cells). Unexpectedly, FGF2 supported adhesion of both αvβ3-K562 and K562 cells to the similar extent, suggesting that FGF2 binds to α5β1 in addition to αvβ3, since α5β1 is the only integrin expressed in K562 cells [20]. It was found that the K125 to E mutation (K125E) and K119E/R120E markedly suppressed adhesion of K562 cells to FGF2 (FIG. 1b). The R44E mutation, which corresponds to R50E in FGF1, did not affect integrin binding, suggesting that FGF1 and FGF2 do not bind to integrins in the same manner. Surface plasmon resonance (SPR) study using immobilized soluble αvβ3 indicated that WT FGF2 bound to immobilized soluble αvβ3 on the sensor chip at $K_d$=7.75× $10^{-8}$ M (FIG. 1c). The K125E mutant showed lower affinity ($K_d$=1.1×$10^{-6}$ M) and lower RU than WT FGF2 ($K_d$=7.75× $10^{-8}$ M) (FIG. 1d). The K119E/R120E mutant did not show detectable binding to αvβ3 in SPR. K119E/R120E was defective in binding to heparin, but K125E of FGF2 bound to heparin (data not shown). These findings are consistent with the docking model and K125E and K119E/R120E in the predicted integrin-binding site of FGF2 suppress FGF2 binding to integrin αvβ3 and α5β1. This does not rule out the possibility, however, that substitution of these residues indirectly affects integrin binding through global conformational changes.

Figure 2A:
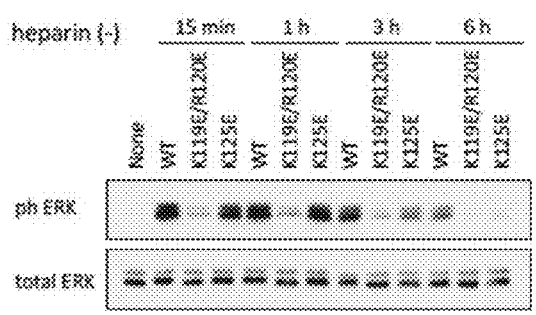
FIGS. 2A-2B. FGF2 mutants are defective in activating Erk1/2 and inducing DNA synthesis and suppress DNA synthesis induced by WT FGF2 in NIH3T3 mouse embryonic fibroblasts. NIH3T3 cells were stimulated with either WT FGF2 (5 ng/ml) or FGF2 mutants (each 5 ng/ml) for indicated periods. Cell lysates were analyzed by western blotting using anti-phosphorylated ERK1/2 and total ERK1/2 (FIG. 2A). NIH3T3 cells were starved and stimulated with WT FGF2 (5 ng/ml), FGF2 mutants (5 ng/ml) or the mixture of WT FGF2 (5 ng/ml) and mutants (250 ng/m) for 24 in the presence of BrdU (FIG. 2B). Results are expressed as means +/−SE of the absorbance.

K119E/R120E and K125E FGF2 Mutants are Defective in ERK1/2 Activation and in Inducing DNA Synthesis and Suppress DNA Synthesis Induced by WT FGF2 in NIH3T3 Cells To study the role of integrin binding to FGF2 in FGF2 signaling, it was tested if K119E/R120E and K125E could induce ERK1/2 phosphorylation in NIH3T3 cells. Since sustained ERK1/2 activation (>3 hrs after stimulation) is integrin-dependent and crucial to cell cycle entry upon FGF stimulation [21, 22]. It was found that WT FGF2-induced ERK1/2 phosphorylation sustained until 3 h, while K125E-induced ERK1/3 activation diminished after 3 h. K119E/R120E was not able to induce transient or sustained ERK1/2 at all (FIG. 2A). These results suggest that K119E/R120E and K125E were both defective in inducing sustained ERK1/2 activation, as in the case of the R50E mutant of FGF1, which induces transient ERK1/2 activation but is defective in sustained ERK1/2 activation [11].

Figure 2B:
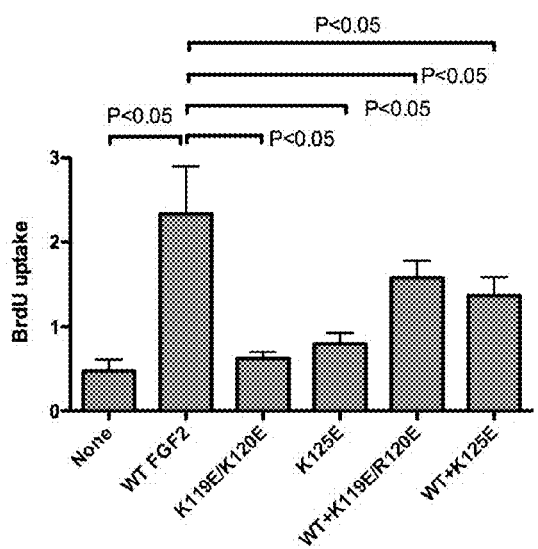

It was further tested if K119E/R120E and K125E could induce DNA synthesis using BrdU incorporation assays in NIH3T3 cells. It was found that K119E/R120E and K125E were both defective in inducing DNA synthesis (FIG. 2B), consistent with the report that DNA synthesis is related to sustained ERK1/2 activation and the ability of FGF2 to bind to integrins [21, 22]. Notably, excess FGF2 mutants suppressed WT FGF2-induced DNA synthesis (FIG. 2B), suggesting that K119E/R120E and K125E are dominant-negative.

K119E/R120E and K125E FGF2 Mutants are Defective in Inducing ERK1/2 Activation and Cell Migration in Human Umbilical Endothelial Cells (HUVEC) and Suppress HUVEC Migration Induced by WT FGF2

Figure 3A:
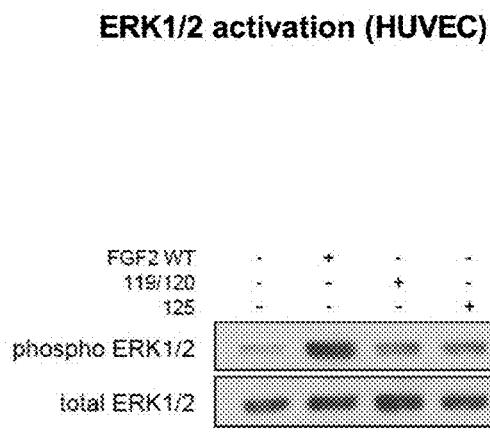
FIGS. 3A-3B. FGF2 mutants are defective in inducing cell migration and suppress cell migration induced by WT FGF2 in HUVECs.
Figure 3B:
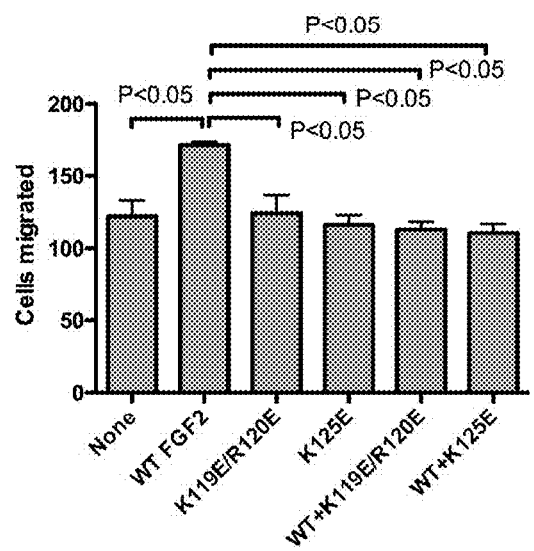

The ability of K119E/R120E and K125E to suppress FGF2 signaling was tested in human umbilical endothelial cells (HUVEC). It was found that WT FGF2 induced ERK1/2 phosphorylation in HUVECs, but K119E/R120E and K125E did not (FIG. 3A), suggesting that the FGF2 mutations affect FGF2 signaling in HUVECs as in NIH3T3 cells. Endothelial cell migration is a critical feature of tumor angiogenesis. The effect of the FGF2 mutants on migration of HUVECs was examined. It was found that WT FGF2 induced migration of HUVECs, but K119E/R120E or K125E did not (at 5 ng/ml) (FIG. 3B). Excess mutants effectively suppressed migration of HUVECs increased by WT FGF2 (FIG. 3B). This suggests that K119E/R120E and K125E act as antagonists of FGF2 in migration of HUVECs.

K119E/R120E and K125E FGF2 Mutants are Defective in Angiogenesis and Suppress Angiogenesis Induced by WT FGF2

It was then tested if K119E/R120E and K125E FGF2 mutants could induce angiogenesis and if they could suppress angiogenesis induced by WT FGF2 using three different angiogenesis models.

Figure 4A:
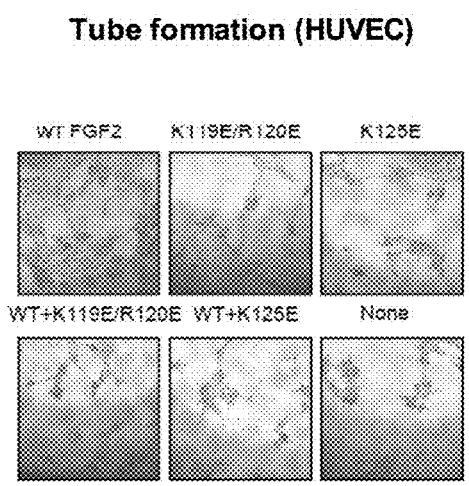
FIGS. 4A-4B. FGF2 mutants are defective in inducing tube formation and suppress tube formation induced by WT FGF2 in HUVECs.
Figure 4B:
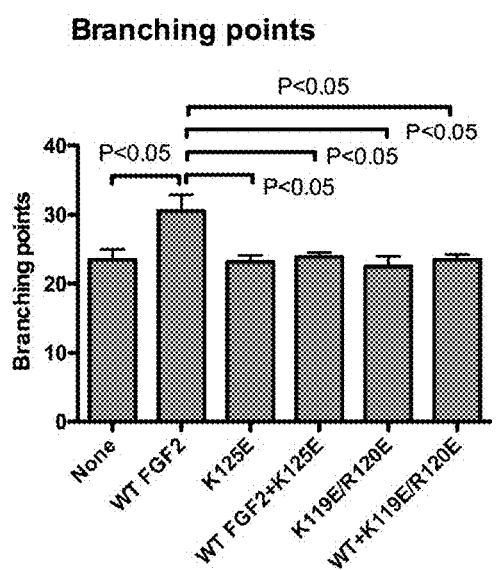

In vitro Tube formation The levels of tube formation were assessed by counting the number of branching points in endothelial tube formation assays. Tube formation induced by K119E/R120E and K125E are significantly less than that induced by WT FGF2 (at 5 ng/ml FGF2) (FIGS. 4a and 4b). The tube-like structures induced by K119E/R120E and K125E were thin and weak as compared with that induced by WT FGF2 (FIG. 4A). Excess K119E/R120E and K125E (at 250 ng/ml) effectively suppressed tube formation induced by WT FGF2 to the background level (FIG. 4B). This indicates that K119E/R120E and K125E directly affect endothelial cell tube formation.

Figure 5A:
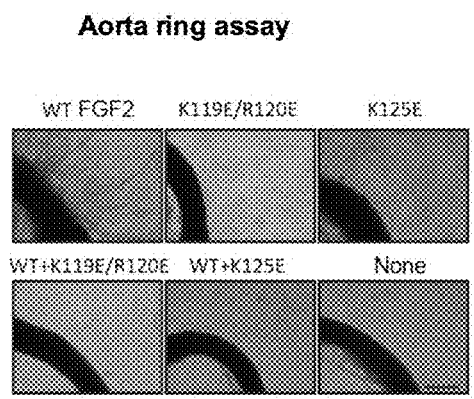
FIGS. 5A-5B. FGF2 mutants suppress WT FGF2-induced vessel sprouting from aorta ring.
Figure 5B:
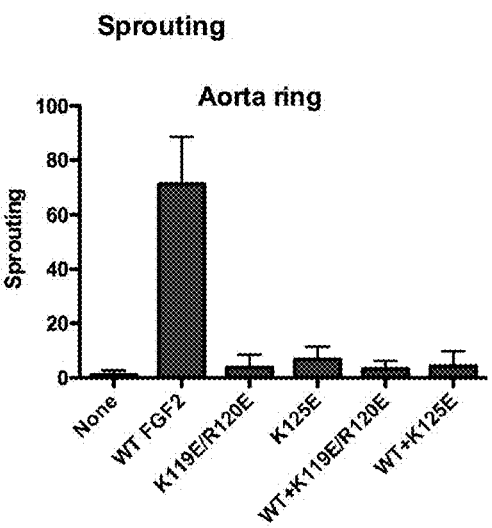

Ex vivo Aorta sprouting assays Isolated rat thoracic aortic ring was embedded in collagen gels in DMEM containing WT FGF2, K119E/R120E, K125E or the mixture of WT FGF2 and excess mutants. WT FGF2 (50 ng/ml) markedly induced the sprouting vessels from aortic arch, but the FGF2 mutants (50 ng/ml) did not (FIG. 5). Excess K119E/R120E and K125E suppressed the sprouting induced by WT FGF2 to the background levels, suggesting that K119E/R120E and K125E are potent antagonists to FGF2-induced ex vivo angiogenesis.

Figure 6A:
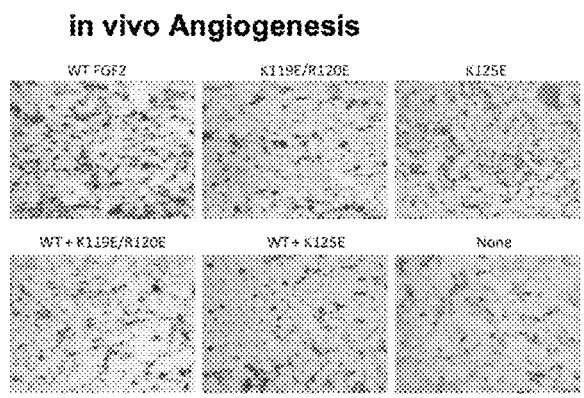
FIGS. 6A-6B. FGF2 mutants suppress WT FGF2-induced angiogenesis.
Figure 6B:
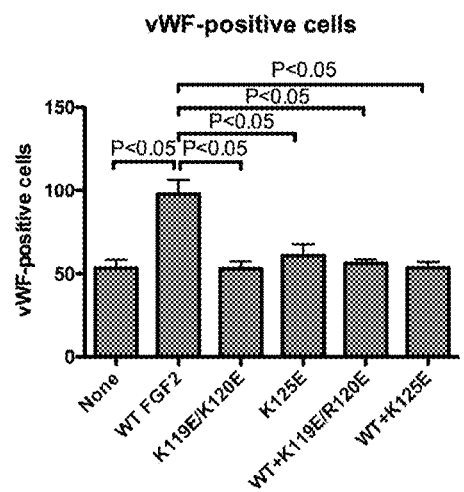

In vivo angiogenesis assays Hydrogels that contain WT FGF2, FGF2 mutants, or the mixture of WT FGF2 and excess FGF2 mutants were implanted subcutaneously into the back of rat. The von Willebrand factor-positive cells in tissue section were counted to detect blood vessels. It was found that WT FGF2 markedly increased the number of blood vessels, whereas FGF2 mutants were defective in this function (FIG. 6). Excess FGF2 mutants reduced the number of blood vessel formation induced by WT FGF2. These findings suggest that K119E/R120E and K125E are antagonists of in vivo angiogenesis induced by WT FGF2.

Taken together, these results indicate that K119E/R120E and K125E FGF2 mutants are potent anti-angiogenic agents in three different angiogenesis assays.

Discussion

The present study establishes that substituting Lys-119/Arg-120, and Lys-125 of FGF2 to Glu effectively reduced the binding of FGF2 to integrins. The positions of key residues for integrin binding in FGF2 are not identical with that in FGF1 (Arg-50), suggesting that FGF2 and FGF1 interact with integrins differently, while the structures of FGF1 and FGF2 are superimposable, and the direct binding to integrins is equally critical for both FGF1 and FGF2. It has previously been proposed that the Asp-Gly-Arg (DGR) motif (residues 37-39) in FGF2 is involved in integrin binding [15]. The DGR motif is close to or within the predicted integrin-binding interface of FGF2, but the R39E mutation did not affect integrin binding. This suggests that the DGR motif may not important for integrin binding. Importantly, the integrin-binding defective FGF2 mutants (K119E/R120E and K125E) are defective in signaling functions (DNA synthesis, sustained ERK1/2 activation, and cell migration). Furthermore, they are dominant-negative antagonists of FGF2 signaling and potently suppressed WT FGF2-induced DNA synthesis, ERK1/2 activation, and cell migration. These results suggest that the direct binding of FGF2 to integrins is involved in FGF2 signaling, as in the case of FGF1. The K119E and R120E mutations have been individually introduced to FGF2, but these mutations only partially reduced integrin binding, and did not affect FGF2 signaling (data not shown). Therefore, substitution of both K119 and R120, such as to Glu, simultaneously result in optimal reduction in FGF2 signaling.

Notably, K119E/R120E and K125E FGF2 potently suppressed WT FGF2-induced angiogenesis in vitro (tube formation), ex vivo (aorta ring assays), and angiogenesis in vivo. These findings indicate that they are potent anti-angiogenic agents. K119E/R120E and K125E are comparable as inhibitors of angiogenesis. It has been proposed that the thermal stability of FGF2 is a major reason why FGF2 is involved in so many more biological processes than FGF1 and why FGF2 is a determinant factor in regulating self-renewal, differentiation, reprogramming in human pluripotent stem cells [23]. The consequence of high stability of FGF2 is a long half-life in vivo (7.6 h) [3]. Since FGF2 binds to all FGFR isoforms [24], it is likely that K119E/R120E and K125E FGF2 mutants will be theoretically able to suppress signaling from all members of the FGF family as in the case of FGF1. Therefore, it is likely that K119E/R120E and K125E FGF2 mutants are potentially useful to suppress biological or pathological events that include FGF signaling. Since K125E bound to heparin and K119E/R120E did not, it is likely that the ability to bind heparin may not be directly related to their dominant-negative actions.

Potential advantage of the FGF2 mutants is that, first, they are highly specific to FGFR compared to tyrosine kinase inhibitors, which are selective rather than specific. Second, FGF2 mutants are small in size compared to IgG, and therefore FGF2 mutants have better penetrance (access to) to diseased tissues. Third, currently used targeting therapeutics (antibodies and kinase inhibitors) almost always induce resistance. This is partly due to point mutations in antibody epitopes or inhibitor-binding sites. Cancer cells obviously benefit from mutations that block the binding of antagonists. It is believed that K119E/R120E and K125E of FGF2 may not induce such mutations in FGFR because the FGF2 mutants bind to FGFR exactly the same way as WT FGF2, and blocking binding of FGF2 (and other members of the FGF family) to FGFR would not benefit cancer cells.

The specifics of the role of integrins in FGF signaling are unclear. $\alpha v\beta 3$ integrin is highly expressed in endothelium during angiogenesis and is involved in neovascularization induced by FGF2 [25, 26]. Previous studies found that the binding of FGF2 to FGFR is not sufficient to induce cell proliferation in endothelial cells and that an interaction of FGF2 with a cell surface integrin receptor is also required [15]. This is consistent with the observation that anti-αvβ3 antibody inhibited the angiogenic activity exerted in vivo by FGF2 without affecting neovascularization induced by vascular endothelial cell growth factor, transforming growth factor-α, or phorbol ester [26]. The current study also suggests that integrins other than αvβ3 may bind to FGF2. If this is the case antagonists to multiple integrins are needed to block FGF2-integrin interaction. It would be necessary to address the integrin binding specificity of FGF2 in details in future studies. On the other hand, it is likely that the K119E/R120E and K125E mutations suppress binding to multiple integrins regardless of integrin species. If this is the case the FGF2 mutants may be more effective than antagonists for individual integrins. The integrin-binding defective FGF2 mutants will be useful to study the molecular details of the FGF2/FGFR/integrin crosstalk.

It remains to be confirmed that other members of the FGF family also require integrin binding for their signaling functions in future studies. In such case dominant-negative inhibitors of FGFs may be generated by generating integrin-binding defective mutants.

TABLE 1

Amino acid residues of FGF2 and αvβ3 that are in the predicted interface

| FGF2 | αv | β3 |
|---|---|---|
| Asn-27, Arg-39, Glu-78, Asp-79, Gly-80, Lys-110, Tyr-111, Thr-112, Ser-113, Trp-114, Lys-119, Arg-120, Thr-121, Gln-123, Tyr-124, Lys-125, Leu-126, Ser-128, Lys-129, Thr-130, Gly-131, Pro-132, Gly-133, Gln-134 | Met-118, Gln-145, Asp-146, Ile-147, Asp-148, Ala-149, Asp-150, Gly-151, Phe-177, Tyr-178, Trp-179, Gln-180, Thr-212, Ala-213, Gln-214, Ala-215, Ile-216, Asp-218, Asp-219, Arg-248 | Tyr122, Ser-123, Met-124, Lys-125, Asp-126, Asp-127, Asp-179, Met-180, Lys-181, Thr-182, Arg214, Arg-216, Asp-217, Ala-218, Asp-251, Lys-253, Thr-311, Glu-312, Asn-313, Val-314, Ser-334, Met-335, |

Amino acid residues in integrin αvβ3 and FGF2 within 6 Å to each other in the docking model were identified using Swiss-pdb viewer v. 4.1.

All patents, patent applications, and other publications cited in this application, including published amino acid or polynucleotide sequences, are incorporated by reference in the entirety for all purposes.

REFERENCES

1 Lanner, F. and Rossant, J. (2010) The role of FGF/Erk signaling in pluripotent cells. Development. 137, 3351-3360

2 Guillemot, F. and Zimmer, C. (2011) From cradle to grave: the multiple roles of fibroblast growth factors in neural development. Neuron. 71, 574-588

3 Beenken, A. and Mohammadi, M. (2009) The FGF family: biology, pathophysiology and therapy. Nat Rev Drug Discov. 8, 235-253

4 Hynes, R. O. (2002) Integrins: bidirectional, allosteric signaling machines. Cell. 110, 673-687

5 Takada, Y., Ye, X. and Simon, S. (2007) The integrins. Genome Biol. 8, 215

6 Brooks, P. C., Clark, R. A. and Cheresh, D. A. (1994) Requirement of vascular integrin alpha v beta 3 for angiogenesis. Science. 264, 569-571

7 Eliceiri, B. P. (2001) Integrin and growth factor receptor crosstalk. Circ Res. 89, 1104-1110

8 Kim, S. H., Turnbull, J. and Guimond, S. (2011) Extracellular matrix and cell signalling: the dynamic cooperation of integrin, proteoglycan and growth factor receptor. J Endocrinol. 209, 139-151

9 Odenthal, J., Takes, R. and Friedl, P. (2016) Plasticity of tumor cell invasion: governance by growth factors and cytokines. Carcinogenesis. 37, 1117-1128

10 Desgrosellier, J. S. and Cheresh, D. A. (2010) Integrins in cancer: biological implications and therapeutic opportunities. Nat Rev Cancer. 10, 9-22

11 Mori, S., Wu, C. Y., Yamaji, S., Saegusa, J., Shi, B., Ma, Z., Kuwabara, Y., Lam, K. S., Isseroff, R. R., Takada, Y. K. and Takada, Y. (2008) Direct Binding of Integrin {alpha}v{beta}3 to FGF1 Plays a Role in FGF1 Signaling. J Biol Chem. 283, 18066-18075

12 Mori, S. and Takada, Y. (2013) Crosstalk between Fibroblast Growth Factor (FGF) Receptor and Integrin through Direct Integrin Binding to FGF and Resulting Integrin-FGF-FGFR Ternary Complex Formation. Medical Sciences. 1, 20-36

13 Yamaji, S., Saegusa, J., Ieguchi, K., Fujita, M., Takada, Y. K. and Takada, Y. (2010) A novel fibroblast growth factor-1 (FGF1) mutant that acts as an FGF antagonist. PLoS One. 5, e10273

14 Mori, S., Tran, V., Nishikawa, K., Kaneda, T., Hamada, Y., Kawaguchi, N., Fujita, M., Takada, Y. K., Matsuura, N., Zhao, M. and Takada, Y. (2013) A Dominant-Negative FGF1 Mutant (the R50E Mutant) Suppresses Tumorigenesis and Angiogenesis. PLoS One. 8, e57927

15 Rusnati, M., Tanghetti, E., Dell'Era, P., Gualandris, A. and Presta, M. (1997) alphavbeta3 integrin mediates the cell-adhesive capacity and biological activity of basic fibroblast growth factor (FGF-2) in cultured endothelial cells. Mol Biol Cell. 8, 2449-2461

16 Saegusa, J., Akakura, N., Wu, C. Y., Hoogland, C., Ma, Z., Lam, K. S., Liu, F. T., Takada, Y. K. and Takada, Y. (2008) Pro-inflammatory secretory phospholipase A2 type IIA binds to integrins alphavbeta3 and alpha4beta1 and induces proliferation of monocytic cells in an integrin-dependent manner. J Biol Chem. 283, 26107-26115

17 Wu, P. L., Lee, S. C., Chuang, C. C., Mori, S., Akakura, N., Wu, W. G. and Takada, Y. (2006) Non-cytotoxic cobra cardiotoxin A5 binds to alpha(v)beta3 integrin and inhibits bone resorption. Identification of cardiotoxins as non-RGD integrin-binding proteins of the Ly-6 family. J Biol Chem. 281, 7937-7945

18 Fujita, M., Ieguchi, K., Cedano-Prieto, D. M., Fong, A., Wilkerson, C., Chen, J. Q., Wu, M., Lo, S. H., Cheung, A. T., Wilson, M. D., Cardiff, R. D., Borowsky, A. D., Takada, Y. K. and Takada, Y. (2013) An Integrin Binding-defective Mutant of Insulin-like Growth Factor-1 (R36E/R37E IGF1) Acts as a Dominant-negative Antagonist of the IGF1 Receptor (IGF1R) and Suppresses Tumorigenesis but Still Binds to IGF1R. J Biol Chem. 288, 19593-19603

19. Fujita, M., Takada, Y. K. and Takada, Y. (2012) Integrins alphavbeta3 and alpha4beta1 Act as Coreceptors for Fractalkine, and the Integrin-Binding Defective Mutant of Fractalkine Is an Antagonist of CX3CR1. J Immunol. 189, 5809-5819
20. Hemler, M. E., Huang, C. and Schwarz, L. (1987) The VLA protein family. Characterization of five distinct cell surface heterodimers each with a common 130,000 molecular weight beta subunit. J Biol Chem. 262, 3300-3309
21. Eliceiri, B. P., Klemke, R., Stromblad, S. and Cheresh, D. A. (1998) Integrin alphavbeta3 requirement for sustained mitogen-activated protein kinase activity during angiogenesis. J Cell Biol. 140, 1255-1263
22. Sharrocks, A. D. (2006) Cell cycle: sustained ERK signalling represses the inhibitors. Curr Biol. 16, R540-542
23. Chen, G., Gulbranson, D. R., Yu, P., Hou, Z. and Thomson, J. A. (2012) Thermal stability of fibroblast growth factor protein is a determinant factor in regulating self-renewal, differentiation, and reprogramming in human pluripotent stem cells. Stem Cells. 30, 623-630
24. Ornitz, D. M., Xu, J., Colvin, J. S., McEwen, D. G., MacArthur, C. A., Coulier, F., Gao, G. and Goldfarb, M. (1996) Receptor specificity of the fibroblast growth factor family. J Biol Chem. 271, 15292-15297
25. Brooks, P. C., Montgomery, A. M., Rosenfeld, M., Reisfeld, R. A., Hu, T., Klier, G. and Cheresh, D. A. (1994) Integrin alpha v beta 3 antagonists promote tumor regression by inducing apoptosis of angiogenic blood vessels. Cell. 79, 1157-1164
26. Friedlander, M., Brooks, P. C., Shaffer, R. W., Kincaid, C. M., Varner, J. A. and Cheresh, D. A. (1995) Definition of two angiogenic pathways by distinct alpha v integrins. Science. 270, 1500-1502

What is claimed is:

1. A composition comprising: (1) a polypeptide comprising the amino acid sequence of SEQ ID NO:1, wherein the amino acid sequence of SEQ ID NO:1 has (A) an E substitution at K119 and an E substitution at R120 or (B) an E substitution at K125, and wherein the polypeptide suppresses FGF2 signaling; (2) an anti-angiogenic agent; and (3) a physiologically acceptable carrier.

2. The composition of claim 1, wherein the polypeptide consists of the amino acid sequence of SEQ ID NO:1, and wherein the amino acid sequence of SEQ ID NO:1 has (A) an E substitution at K119 and an E substitution at R120 or (B) an E substitution at K125.

3. The composition of claim 2, wherein the amino acid sequence of SEQ ID NO:1 has an E substitution at K125.

4. The composition of claim 2, wherein the amino acid sequence of SEQ ID NO:1 has an E substitution at K119 and an E substitution at R120.

5. The composition of claim 1, wherein the amino acid sequence of SEQ ID NO:1 has an E substitution at K119 and an E substitution at R120.

6. The composition of claim 1, wherein the amino acid sequence of SEQ ID NO:1 has an E substitution at K125.

7. The composition of claim 1, wherein the polypeptide further comprises at least one heterologous amino acid sequence at the N- and/or C-terminus of the amino acid sequence of SEQ ID NO: 1.

8. A method for suppressing FGF2 signaling in a mammal, comprising administering to the mammal an effective amount of the composition of claim 1.

9. The method of claim 8, wherein the composition is administered orally.

10. The method of claim 8, wherein the composition is administered topically.

11. The method of claim 8, wherein the composition is administered intravenously.

12. The method of claim 8, wherein the mammal has a vascularized solid tumor or metastases from a primary tumor.

13. The method of claim 8, wherein the mammal is a human.

14. A kit for suppressing FGF signaling, comprising (1) a polypeptide comprising the amino acid sequence of SEQ ID NO:1, wherein the amino acid sequence of SEQ ID NO:1 has (A) an E substitution at K119 and an E substitution at R120 or (B) an E substitution at K125, and wherein the polypeptide suppresses FGF2 signaling; and (2) an anti-angiogenic agent.

15. The kit of claim 14, further comprising an instruction manual.

* * * * *